United States Patent [19]

Bernady et al.

[11] 4,217,308
[45] Aug. 12, 1980

[54] PROCESS FOR PREPARING N-ALKYLETHYLENEDIAMINES

[75] Inventors: Karel F. Bernady; Paul D. Mogolesko, both of Belle Mead, N.J.

[73] Assignee: American Cyanamid Company, Stamford, Conn.

[21] Appl. No.: 48,337

[22] Filed: Jun. 14, 1979

Related U.S. Application Data

[63] Continuation-in-part of Ser. No. 960,972, Nov. 15, 1978, abandoned, which is a continuation-in-part of Ser. No. 873,450, Jan. 30, 1978, abandoned.

[51] Int. Cl.$^2$ .................. C07C 85/04; C07C 85/26
[52] U.S. Cl. ........................ 260/583 P; 260/583 N
[58] Field of Search .................... 260/583 N, 583 P

[56] References Cited

U.S. PATENT DOCUMENTS 4,061,633  12/1977  Blyakhman et al. ........ 260/583 N X

FOREIGN PATENT DOCUMENTS 2113208  9/1972  Fed. Rep. of Germany ....... 260/583 P

OTHER PUBLICATIONS

Linsker et al., "JACS", vol. 67, pp. 1581–1582, (1945).

Primary Examiner—John Doll
Attorney, Agent, or Firm—Charles F. Costello, Jr.

[57] ABSTRACT

This disclosure describes a novel process for preparing N-alkylethylenediamines which are useful as intermediates for purifying penicillins. N-alkylethylenediamines are also useful for preparing penicillins and cephalosporins. Specifically, N-ethylethylenediamine is useful for manufacturing piperacillin which is useful as an antibiotic.

More particularly, the invention relates to a process for the efficient reaction of an alkyl halide and ethylenediamine and the recovery of anhydrous, ethylenediamine-free N-alkylethylenediamines therefrom.

25 Claims, No Drawings

PROCESS FOR PREPARING N-ALKYLETHYLENEDIAMINES

CROSS-REFERENCE TO RELATED APPLICATIONS

This application is a continuation-in-part of application Ser. No. 960,972 filed Nov. 15, 1978 which is a continuation-in-part of application Ser. No. 873,450 filed Jan. 30, 1978, both now abandoned.

BACKGROUND OF THE INVENTION

The applicants are not aware of any prior art references which, in their respective judgments as a person having ordinary skill in the art, would anticipate or render obvious the process of this invention. However, to fully develop the background and establish the state of the art, the following references are set forth. J. of Pharm. Sciences 57 2073 (1968) discloses the preparation of N-alkylethylenediamines wherein the alkyl is from $C_3$ to $C_5$ by the alkylation of anhydrous ethylenediamine with an alkyl halide in a solvent. Yields of or less than 57% are reported. J.A.C.S. 73 1370 (1951) discloses the preparation of N-alkylethylenediamines wherein the alkyl is from $C_1$ to $C_8$ by reacting an N-alkylamine with 2-bromoethylamine hydrobromide. Yields of or less than 52% are reported. U.S. Pat. No. 2,868,833 discloses the preparation of N-ethylethylenediamine by reacting monoacetylethylenediamine with lithium aluminum hydride in a solvent. Great Britain Pat. No. 1,007,343 discloses the preparation of octadecylethylenediamine by reacting ethylenediamine with octadecyl bromide in a solvent. The solvent is extracted with heptane and the heptane is removed by evaporation. Crude octadecylethylenediamine is obtained in a yield of 96%. There are no examples in the literature which disclose the preparation of N-ethylethylenediamine

(hereinafter referred to as NEED), by the reaction of an ethyl halide and ethylenediamine, (hereinafter referred to as EDA). If EDA and an alkyl halide are reacted and neutralized to continuously prepare and recover the N-alkylethylenediamine, the recovery of pure product in high yield and purity is difficult because of the presence of EDA and water in the neutralized reaction mixture. With N-ethylethylenediamine the reaction mixture is not separable with a 15-plate column at a reflux ratio of 95%. An anhydrous mixture of equal parts by weight of NEED and EDA also is not efficiently separated under the above-identified fractionation conditions. There is a need, therefore, for an efficient process that will provide an N-alkylethylenediamine in a relatively high yield and purity.

SUMMARY OF THE INVENTION

In accordance with the present invention, there is provided a process for preparing N-alkylethylenediamines wherein the alkyl is from $C_2$ to about $C_6$. An alkyl halide is reacted with EDA at a temperature of from about $-10°$ C. to about $120°$ C. and at a mole ratio of EDA to said alkyl halide of about 1–20:1, in the presence of about 0–50% by weight of water, to form a reaction mixture containing N-alkylethylenediamine. The resulting reaction mixture is then contacted with an aqueous alkalizing agent to form a mixture consisting of an inorganic halide, an aqueous phase, and an organic phase, from which the organic phase is separated. The organic layer is diluted with about 0.02–100% by weight of a suitable hydrocarbon solvent and the resulting mixture is azeotropically fractionally distilled to remove all the water and unreacted EDA therefrom. The resulting reaction mixture is then fractionally distilled to remove residual hydrocarbon solvent and recover the N-alkylethylenediamine in a purity greater than about 99%.

Preferably, the reaction between the alkyl halide and the EDA is carried out at about $25°–50°$ C. in the presence of about 0–30% by weight of water and at a mole ratio of EDA to alkyl halide of about 2–5:1. The resulting reaction mixture is then contacted with an aqueous caustic soda and the organic layer is diluted with about 0.02–20% by weight of the hydrocarbon solvent before carrying out the distillation.

The process of the subject invention can be modified by the additional steps of: (1) recovering and recycling aqueous EDA from the azeotrope, (2) recovering and recycling the hydrocarbon solvent, and (3) contacting the separated, alkalized aqueous layer with about 10–100% by weight of said hydrocarbon solvent based on the weight of said organic layer, separating the extracted aqueous layer and diluting the organic layer with the hydrocarbon extract before proceeding with the azeotropic fractional distillation.

The present invention also provides processes for the removal of water and/or EDA from the N-alkylethylenediamine by adding a suitable hydrocarbon solvent thereto, azeotropically fractionally distilling the water and/or EDA therefrom, and fractionally distilling to remove residual hydrocarbon solvent and recover anhydrous and/or EDA-free, N-alkylethylenediamine. The advantages of the process of the present invention over previously available processes are that (1) the final product has a purity greater than about 99%; and (2) the process results in high yields and high productivity.

In accordance with the present invention there is also provided an alternative process for preparing N-alkylethylenediamine of about 99% purity comprising (a) reacting an alkyl halide and EDA at a mole ratio of EDA to said alkyl halide of about 1–20:1 and a temperature of about $-10°$ C. to about $120°$ C. under anhydrous conditions to obtain an alkylation reaction mixture; (b) adding thereto about 0.02–30% by weight of a suitable hydrocarbon solvent, based on the weight of said alkylation reaction mixture; (c) fractionally distilling a mixture of EDA and said hydrocarbon solvent therefrom to essentially remove EDA from the resulting mixture; (d) neutralizing the resulting reaction mixture by contacting it with at least 0.9 molecular equivalent of a suitable alkalizing agent per mole of said alkyl halide to form a slurry of an alkali halide precipitate; (e) separating said alkali halide from said slurry and recovering the resulting mother liquor therefrom; (f) washing said separated alkali halide with said hydrocarbon solvent; (g) azeotropically fractionally distilling a combination of said mother liquor from step (e) plus recovered hydrocarbon wash liquor from step (f) to remove essentially all water and residual EDA from the resulting mixture; and (h) fractionally distilling the resulting reaction mixture to remove residual hydrocarbon solvent and recover said N-alkylethylenediamine.

DESCRIPTION OF PREFERRED EMBODIMENTS

EDA, either as an anhydrous liquid or containing water, and an alkyl halide, preferably an alkyl chloride, are admixed in a suitable reactor vessel while agitating and maintaining the reaction mixture at from about −10° C. to about 120° C. (preferably at about 25°–50° C.), over a period of about 5–15 hours (preferably about 7–9 hours), to provide a mole ratio of EDA to alkyl halide of about 1–20:1 (preferably about 2–5:1) and form a reaction mixture containing about 0–50% by weight of water (preferably about 0–30%). Suitable alkyl halides include ethyl chloride, ethyl bromide, and ethyl iodide, propyl chloride, isopropyl chloride, butyl chloride, pentyl chloride, 1-hexyl chloride, and 3-hexyl chloride. The total residence time in the reactor vessel depends on the temperature employed, with shorter residence times employed with higher temperatures.

The reaction mixture is then vigorously contacted with an aqueous solution of an alkalizing agent to form a mixture, consisting of an organic layer, an aqueous layer, and an alkaline halide. Sufficient alkalizing agent is employed so that the pH of the aqueous layer does not go below about 7, preferably not below 8 and an aqueous layer is formed. Suitable alkalizing agents include sodium and potassium hydroxide, either singly or in mixtures. The preferred alkalizing agent is about 50% aqueous sodium hydroxide.

The organic layer is separated from the alkaline halide and the aqueous layer by making a phase separation, or by first separating the alkaline halide by filtration or centrifugation, and then making a phase separation. The organic layer contains the N-alkylethylenediamine, unreacted EDA, and higher alkylation products such as N,N'-dialkylethylenediamine, N,N-dialkylethylenediamine, N,N,N'-trialkylethylenediamine, and N,N,N',N'-tetraalkylethylenediamine. The organic layer is then diluted with about 0.02–100% by weight, preferably about 0.02–20% by weight, of a suitable hydrocarbon solvent, based on the weight of said organic layer.

Preferably, the separated aqueous layer is extracted with aout 10–100% by weight, preferably about 10–20% by weight, of said suitable hydrocarbon solvent, based on the weight of said organic layer and the two-phase mixture is allowed to settle. The extracted aqueous layer is then separated and the hydrocarbon solvent extract is used to dilute the above-mentioned organic layer.

As employed herein, the term "suitable hydrocarbon solvent" is defined as a hydrocarbon solvent which forms an azeotrope with water and/or EDA below the boiling point of the product N-alkylethylenediamine from which condensed azeotrope water and/or EDA may be separated from the hydrocarbon without inclusion of substantial amount of the N-alkylethylenediamine. Suitable hydrocarbon solvents include n-heptane, isooctane, cyclohexane, n-hexane, methylcyclohexane, n-pentane, and the like, although the preferred hydrocarbon solvent is n-heptane.

The diluted organic layer is then heated to boiling through a distillation column to azeotropically fractionally distill off any residual EDA and water. After allowing the distillate to settle, the lower EDA-water layer may be separated and recycled to the alkylation vessel, and the upper hydrocarbon layer may be recycled to the distillation column until anhydrous EDA-free N-alkylethylenediamine is obtained, or transferred to a vessel for extraction of the original aqueuos layer.

The residual EDA-free reaction mixture, containing N-alkylethylenediamine, higher alkylated ethylenediamines, and the hydrocarbon solvent is now fractionally distilled, using a fractionation column containing sufficient theoretical plates, to separate said hydrocarbon solvent from the N-alkylethylenediamine. For example, using a column containing 15 theoretical plates and n-heptane as the solvent, the n-heptane distills off as a forerun boiling at about 98°–100° C. The forerun of hydrocarbon solvent so obtained may be recycled to other stages of the process, such as dilution of the organic layer, azeotroping EDA and water from the reaction mixture, or extracting the aqueous layer, as described above.

After removal of the forerun of hydrocarbon solvent, the distillation is continued to obtain the N-alkylethylenediamine (purity greater than 99%) in a yield of greater than 60% based on the alkyl halide charged. The procedure employed herein may also be used to remove water and/or EDA from the N-alkylethylenediamine by adding a suitable amount of said hydrocarbon solvent thereto, azeotropically fractionally distilling the water or EDA, or both, therefrom and fractionally distilling the residue to remove excess hydrocarbon solvent and obtain anhydrous, EDA-free N-alkylethylenediamine. It is to be understood that the aforedescribed process may also be carried out continuously using appropriate vessels, such as continuous flow reactors, splitter vessels, distillation columns, and the like.

In an alternative process ethylenediamine as an anhydrous liquid, is reacted with an alkyl halide as shown below

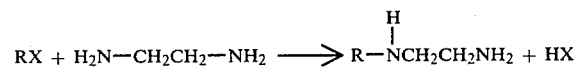

wherein X is a halo atom, such as chloro, bromo, or iodo, preferably chloro. The reaction is carried out while agitating the reaction mixture in a suitable reactor vessel at about −10° C. to about 120° C., preferably at about 25°–75° C., over a period of about 1–24 hours, preferably about 2–6 hours. The mole ratio of EDA to the alkyl halide employed is about 1–20 to 1, preferably about 2–5 to 1. The total residence time in the reactor vessel will depend on the temperature employed, with shorter residence times employed with higher temperatures.

Upon completion of the reaction, the reaction mixture is diluted with about 0.02–30% by weight, preferably about 0.5–1.0% by weight, of a suitable hydrocarbon solvent, based on the weight of the reaction mixture. As employed herein the term "suitable hydrocarbon solvent" has the same meaning as previously defined. The diluted reaction mixture is then heated to boiling through a distillation column to azeotropically fractionally distill off any residual EDA. Optionally, the EDA distillate may be recovered and recycled.

Suitable hydrocarbon solvents include n-heptane isooctane, cyclohexane, n-hexane, methylcyclohexane, n-pentane, and the like, although the preferred hydrocarbon solvent is n-heptane.

The reaction mixture is then neutralized by contacting it with at least 0.9 molecular equivalent of a suitable alkalizing agent per mole of alkyl halide used. As employed herein the term "suitable alkalizing agent" is defined as sodium or potassium hydroxide, either singly or in mixtures. The preferred alkalizing agent is 50% aqueous sodium hydroxide.

The resulting alkali halide precipitate is separated from the resulting slurry by conventional means, such as filtration or centrifugation, and washed with the hydrocarbon solvent described previously, preferably with n-heptane.

The hydrocarbon solvent wash liquors are collected and combined with the mother liquor obtained by the separation of the alkali halide precipitate from the slurry formed by the addition of an alkalizing agent to the reaction mixture. The combined liquors are azeotropically fractionally distilled at atmospheric pressure through a packed column, preferably with recycle of heptane distillate to the column, until the residual material is essentially free of EDA and water.

The resulting essentially EDA-free reaction mixture, containing the product N-alkylethylenediamine, higher alkylated ethylenediamines, and the hydrocarbon solvent is now fractionally distilled, using a fractionation column containing sufficient theoretical plates, to separate said hydrocarbon solvent from the product N-alkylethylenediamine. For example, using a column containing 15 theoretical plates, n-heptane distills off as a forerun boiling at aout 98°–100° C. The forerun of hydrocarbon solvent so obtained may be recycled to other stages of the process, such as dilution of the reaction mixture, or azeotroping EDA or water from the reaction mixture.

After removal of the forerun of hydrocarbon solvent the reaction mixture is preferably clarified to remove any insolubles and distillation of the clarified solution is continued to obtain the N-alkylethylenediamine in a purity greater than 99% and a yield of greater than 60% of theoretical based on the alkyl halide charged.

It is to be understood that the aforedescribed process may also be carried out continuously using appropriate vessels, such as continuous flow reactors, separation vessels, distillation columns, and the like.

The following examples are provided to illustrate the invention. Except as otherwise noted, all parts are by weight and all ranges are inclusive of both numbers. The purity of the product is expressed as area percent, as determined by vapor phase chromatography (VPC).

EXAMPLE 1

This example illustrates the use of anhydrous EDA

Ethyl chloride (565 grams; 8.76 moles) is added to anhydrous EDA (1420 grams; 23.63 moles) at 30°–40° C. over a period of 5 hours. The reaction mixture is stirred for 2 hours after the addition is completed and 50% caustic soda (935 ml; 17.5 moles) is added thereto. The resulting mixture is stirred for 30 minutes, allowed to settle, and the aqueous salt slurry is separated and extracted twice with 150 ml of n-heptane. The heptane extracts are added to the organic phase and the combined solution is heated to azeotropically distill water and EDA therefrom at 88°–97° C., using a fractionation column and a splitter device to return distilled heptane to the distillation column and to separate the denser aqueous EDA phase. In this manner an aqueous EDA phase is separated consisting of 394 grams of water and 896 grams of EDA (14.91 moles). The EDA-free residue is fractionally distilled to obtain a heptane forerun (b.p. 98°–102° C.) containing 3–4% by weight of NEED, and 484 grams of NEED (b.p. 130°–131° C.) of greater than 99.8% purity by VPC. The yield is 62.7% of theoretical based on ethyl chloride.

EXAMPLE 2

This example illustrates the use of recovered aqueous EDA

Ethyl chloride (545 grams; 8.45 moles) is added at 30°–40° C. over a period of 5 hours to a mixture of 1245 grams of aqueous EDA recovered from Example 1 (containing 14.39 moles of EDA) and anhydrous EDA (555 grams; 9.23 moles). The reaction mixture is stirred for 2 hours after the addition is completed and 50% caustic soda (902 ml; 16.9 moles) is added thereto. The resulting mixture is processed as described in Example 1 utilizing recovered n-heptane from Example 1 to extract the separated aqueous salt slurry. Fractional distillation of the EDA-free residual material yields a heptane forerun containing 3–4% by weight of NEED, and 483 grams of NEED (b.p. 130°–131° C.) of greater than 99.8% purity by VPC. The yield is 65% of theoretical based on ethyl chloride.

EXAMPLE 3

This example illustrates the separation of EDA from N-Ethylethylenediamine by azeotropic distillation A mixture of EDA (500 grams) and NEED (500 grams) is diluted with 200 ml. of n-heptane and heated to azeotropically fractionally distill (b.p. 87°–90° C.) EDA therefrom, using a distillation column and a device which returns the recovered heptane to the distillation apparatus and allows for the recovery of the denser EDA phase. The EDA thus recovered contains less than 1% NEED by VPC. The EDA-free residue is then fractionally distilled to recover a heptane forerun and pure NEED (b.p. 130°–131° C.).

In the manner described above, substituting cyclohexane, n-hexane, or isooctane for the n-heptane, similar results are obtained.

EXAMPLE 4

This example illustrates the separation of water from N-Ethylethylenediamine by azeotropic distillation To a mixture of 56 grams of NEED and 10 grams of water is added 50 ml. of n-heptane. The mixture is heated to boiling and the water is azeotropically fractionated (b.p. 88°–98° C.) therefrom using a distillation column and a splitter apparatus which returns the recovered heptane to the distillation apparatus and allows for the removal of the denser water phase. After removal of the water is complete, the residue is fractionally distilled to recover a heptane forerun and NEED (b.p. 130°–131° C.) containing less than 0.2% water by VPC.

In the manner described above, substituting cyclohexane, n-hexane, or isooctane for the n-heptane, similar results are obtained.

Examples 5 to 10 illustrate the recovery of N-ethylethylenediamine wherein the EDA is removed before neutralization

EXAMPLE 5

Ethyl chloride (62.4 grams; 0.967 mole) is added to stirred ethylenediamine (146.3 grams; 2.43 moles) over a period of 1 hour while allowing the temperature to rise to 95° C. Upon completion of the addition of the ethyl chloride, n-heptane (34.2 grams) is added thereto and the resulting mixture is azeotropically distilled using a fractionation column and a Dean-Stark device to collect the two-phase liquid distillate consisting of a lower layer of ethylenediamine (85.09 grams) and an upper layer of heptane which is recycled back to the fractionation column until all of the ethylenediamine is removed therefrom.

The remaining material is cooled to 80° C., neutralized with 50% aqueous sodium hydroxide (77.36 grams; 0.967 mole) and the resulting precipitate of sodium chloride is separated by filtration to obtain a filter cake and a two-phase liquid filtrate. The filter cake is then washed with heptane (50 mls) and the washing is added to the original two-phase filtrate.

The resulting two-phase liquid is then azeotropically distilled using a fractionation column and a Dean-Stark device to collect the two-phase distillate consisting of n-heptane and water. After all of the water is removed the residue is fractionally distilled to remove any heptane and recover N-ethylethylenediamine (54.5 grams; b.p. 130°–131° C.; 64% of theoretical) in a purity of 99%.

EXAMPLE 6

The procedure of Example 5 is followed in every detail up to the point of the final distillation. After all the water is removed by azeotropic distillation the residual material is filtered to separate a white precipitate (4.32 grams). The filter cake is then washed with heptane (16 grams) and the washing is combined with the filtrate. The combined filtrate plus washing is then fractionally distilled to remove heptane and recover N-ethylethylenediamine (53.7 grams; b.p. 130°–131° C.; 63% of theoretical) in 99% purity.

EXAMPLE 7

To a glass-lined reactor is charged 848 parts of ethylenediamine (98%) followed by 331 parts of liquid ethyl chloride, charged through a dip leg at a rate to maintain the reaction mixture at 45°–55° C. The mixture is stirred for 2 hours and 91 parts of heptane are added thereto. The excess ethylenediamine is azeotropically distilled off through a packed column with recycle of the heptane distillate to the top of the column. A total of 492 parts of ethylenediamine is recovered from the distillate for recycle. The reaction mixture is neutralized with 402 parts of 50% caustic soda, cooled to room temperature, and centrifuged to remove the sodium chloride by-product. The salt cake is washed with 70 parts of heptane and the wash liquor is combined with the mother liquor in a glass-lined vessel. Water is azeotropically distilled off from the combined liquors through a packed column with recycle of the distilled heptane to the top of the column. After all of the water is removed the heptane is fractionally distilled off through the packed column to obtain a residue containing 273 parts of N-ethylethylenediamine. This residue is reserved for subsequent combination with the residues of Examples 8–10.

EXAMPLE 8

To a glass-lined reactor is charged 492 parts of recovered ethylenediamine from Example 7 and 375 parts of fresh ethylenediamine (98%). To this mixture is charged 331 parts of ethyl chloride at a rate to maintain the reaction mixture at 55°–65° C. The mixture is stirred for 2 hours and 45 parts of recovered heptane from Example 7 are added thereto. The excess ethylenediamine is azeotropically distilled off through a packed column with recycle of the heptane distillate to top of the column. A total of 501 parts of ethylenediamine is recovered from the distillate for recycle. The reaction mixture is neutralized with 407 parts of 50% caustic soda, cooled to room temperature, and centrifuged to remove the sodium chloride by-product. The salt cake is washed with 78 parts of heptane and the wash liquor is combined with the mother liquor in a glass-lined vessel. Water is azeotropically distilled off from the combined liquors through a packed column with recycle of the distilled heptane to the top of the column. After all of the water is removed the heptane is fractionally distilled off through the packed column to obtain a residue containing 288 parts of N-ethylethylenediamine. This residue is reserved for subsequent combination with the residues of Examples 7, 9 and 10.

EXAMPLE 9

To a glass-lined reactor is charged 501 parts of recovered ethylenediamine from Example 8 and 396 parts of fresh ethylenediamine (98%). To this mixture is charged 331 parts of ethyl chloride at a rate to maintain the reaction mixture at 65°–75° C. The mixture is stirred for 2 hours and 28 parts of recovered heptane from Example 8 are added thereto. The excess ethylenediamine is azeotropically distilled off through a packed column with recycle of the heptane distillate to the top of the column. A total of 504 parts of ethylenediamine is recovered from the distillate for recycle. The reaction mixture is neutralized with 409 parts of 50% caustic soda, cooled to room temperature, and centrifuged to remove the sodium chloride by-product. The salt cake is washed with 82 parts of heptane and the wash liquor is combined with the mother liquor in a glass-lined vessel. Water is azeotropically distilled off from the combined liquors through a packed column with recycle of the distilled heptane to the top of the column. After all of the water is removed the heptane is fractionally distilled off through the packed column to obtain a residue containing 310 parts of N-ethylethylenediamine. This residue is reserved for subsequent combination with the residues of Examples 7, 8 and 10.

EXAMPLE 10

To a glass-lined reactor is charged 504 parts of recovered ethylenediamine from Example 9 and 388 parts of fresh ethylenediamine (98%). To this mixture is charged 331 parts of ethyl chloride at a rate to maintain the reaction mixture at 55°–65° C. The mixture is stirred for 2 hours and 30 parts of recovered heptane from Example 9 are added thereto. The excess ethylenediamine is azeotropically distilled off through a packed column with recycle of the heptane distillate to the top of the column. A total of 523 parts of ethylenediamine is recovered from the distillate for recycle. The reaction mixture is neutralized with 409 parts of 50% caustic soda, cooled to room temperature, and centrifuged to remove the sodium chloride by-product. The salt cake is washed with 91 parts of heptane and the wash liquor is combined with the mother liquor in a glass-lined vessel. Water is azeotropically distilled off from the combined liquors through a packed column with recycle of the distilled heptane to the top of the column. After all of the water is removed the heptane is fractionally distilled off through the packed column to obtain a residue containing 317 parts of N-ethylethylenediamine which is combined with the residues of Examples 7, 8 and 9. The resulting material is fractionally distilled through a packed column at atmospheric pressure to obtain 1120 parts of N-ethylethylenediamine, b.p. 129°-131° C. The yield is 61.9% of theoretical based on ethyl chloride.

Examples 11 to 13 illustrate the use of n-propyl halide, isopropyl halide and n-butyl halide, respectively, in the invention

EXAMPLE 11 n-Propyl chloride (327.1 grams; 4.16 moles) is added to anhydrous EDA (988.9 grams; 16.48 moles) at 20°-24° C. over a period of one hour. The reaction mixture is stirred for 4 hours after the addition is completed and 50% caustic soda (392 ml; 7.35 moles) and water (206 mls) are added thereto. The resulting mixture is allowed to settle, and the aqueous salt slurry is separated and extracted twice with 280 ml of n-heptane. The heptane extracts are added to the organic phase and the combined mixture is heated to azeotropically distill water and EDA therefrom at 88°-97° C., using a splitter device to return distilled heptane to the distillation vessel and to separate the denser aqueous EDA phase. The EDA-free residue is then fractionally distilled to obtain a heptane forerun (b.p. 97°-100° C.), and a main fraction of 341.3 grams of N-n-propylethylenediamine (b.p. 75°-77° C. at 60 mm) of greater than 99% purity by VPC. The yield is 79.5% of theoretical based on n-propyl chloride.

Calculated for $C_5H_{14}N_2$: C, 58.77; H, 13.81; N, 27.42. Found: C, 59.08; H, 13.87; N, 27.60.

EXAMPLE 12

Isopropyl chloride (327 grams; 4.16 moles) is added to anhydrous EDA (988.9 grams; 16.48 MOLES) at 70° C. After the addition is completed, the reaction mixture is slowly heated to 100° C., cooled to 25° C., and mixed with 50% caustic soda (391 mls; 7.35 moles) and water (206 mls). The resulting mixture is allowed to settle, and the aqueous salt slurry is separated and extracted twice with 200 mls of n-heptane. The heptane extracts are added to the organic phase and the combined mixture is heated to azeotropically distill water and EDA therefrom at 88°-97° C., using a splitter device to return distilled heptane to the distillation vessel and to separate the denser aqueous EDA phase. The EDA-free residue is then fractionally distilled to obtain a heptane forerun (b.p. 97°-100° C.), and a main fraction of 305 grams of N-isopropylethylenediamine (b.p. 136°-137° C.) of greater than 99% purity by VPC. The yield is 71.1% of theoretical based on isopropyl chloride.

Calculated for $C_5H_{14}N_2$: C, 58.77; H, 13.81; N, 27.42. Found: C, 59.16; H, 13.89; N, 27.28.

EXAMPLE 13 n-Butyl chloride (385.4 grams; 4.16 moles) is added to anhydrous EDA (979.0 grams; 16.29 moles) at 20°-24° C. over a period of one hour. The reaction mixture is stirred at 22°-27° C. for 4 hours after the addition is completed and 50% caustic soda (935 ml; 7.35 moles) and water (207 mls) are added thereto. The resulting mixture is allowed to settle, and the aqueous salt slurry is separated and extracted twice with 200 mls of n-heptane. The heptane extracts are added to the organic phase and the combined mixture is heated to azeotropically distill water and EDA therefrom at 88°-97° C., using a splitter device to return distilled heptane to the distillation vessel and to separate the denser aqueous EDA phase. The EDA-free residue is then fractionally distilled to obtain a heptane forerun (b.p. 96°-100° C.) and a main fraction of 348 grams of N-n-butylethylenediamine (b.p. 74°-77° C. at 20-30 mm) of greater than 99% purity by VPC. The yield is 71.3% of theoretical based on n-butyl chloride.

Calculated for $C_6H_{16}N_2$: C, 62.01; H, 13.88; N, 24.11. Found: C, 61.51; H, 13.92; N, 24.13.

We claim:

1. A process for preparing N-alkylethylenediamine wherein the alkyl is from $C_2$ to about $C_6$ by the alkylation reaction of ethylenediamine (EDA), the improvement comprising: adding a hydrocarbon solvent to the alkylation reaction mixture; and removing, by azeotropic distillation, the unreacted ethylenediamine (EDA) remaining from the alkylation reaction.

2. A process according to claim 1 further characterized in that the reaction mixture is prepared by reacting ethylenediamine with an alkyl halide, and in that the resulting ammonium halide salt is neutralized by reacting it with an aqueous solution of an inorganic alkalizing agent to produce an inorganic halide, an aqueous layer, and an organic layer, said organic layer being separated and being the layer to which the hydrocarbon solvent is added to effect the removal of EDA and water by azeotropic distillation.

3. A process according to claim 2 for preparing an N-alkylethylenediamine comprising reacting ethylenediamine (EDA) and an alkyl halide at a mole ratio of EDA to said alkyl halide of about 1-20:1 and a temperature of from about −10° C. to about 120° C. in the presence of about 0-50% by weight of water to obtain an alkylation reaction mixture; neutralizing said reaction mixture by contacting with an aqueous solution containing about 1-2 molecular equivalents of an inorganic alkalizing agent based on the alkyl halide; separating the inorganic halide and the aqueous layer from the neutralized organic layer and adding to said organic layer about 0.02-100% by weight, based on the weight of said organic layer, of a suitable hydrocarbon solvent; azeotropically fractionally distilling all the EDA and water from the resulting mixture; and fractionally distilling the resulting reaction mixture to remove residual hydrocarbon solvent and recover said N-alkylethylenediamine in a purity greater than about 99%.

4. A process according to claim 3 wherein said EDA and alkyl halide are reacted at a mole ratio of EDA to said alkyl halide of about 2-5:1 and a temperature of about 25°-50° C. in the presence of about 0-30% by weight of water to obtain said alkylation reaction mixture; said reaction mixture is neutralized by contacting with aqueous caustic soda; and about 0.02-20% by weight of said hydrocarbon is added to said organic layer.

5. A process according to claim 3 wherein said hydrocarbon is n-heptane.

6. A process according to claim 4 wherein said hydrocarbon is n-heptane.

7. A process for preparing an N-alkylethylenediamine according to claim 3 including the additional steps of (a) recovering aqueous EDA from the azeotrope and recycling to react with said alkyl halide; and (b) recovering the hydrocarbon solvent from the forerun of the distillation of said N-alkylethylenediamine and recycling to the distillation mixture.

8. A process according to claim 3 with the additional steps of contacting said aqueous layer with 10-100% by weight of said hydrocarbon solvent based on the weight of said organic layer; separating the extracted aqueous layer; and adding the hydrocarbon extract to said organic layer before proceeding with said azeotropic fractional distillation.

9. A process according to claim 7 with the additional steps of contacting said aqueous layer with 10–100% by weight of said recovered hydrocarbon solvent based on the weight of said organic layer; separating the extracted aqueous layer; and adding the hydrocarbon extract to said organic layer before proceeding with said azeotropic fractional distillation.

10. A process according to claims 5 or 6 or 7 or 9 for preparing N-ethylethylenediamine (NEED) wherein said alkyl halide is selected from the group consisting of ethyl chloride, ethyl bromide or ethyl iodide.

11. A process according to claim 10 wherein said alkyl halide is ethyl chloride.

12. A process for separating an N-alkylethylenediamine from an anhydrous mixture of said N-alkylethylenediamine and EDA which comprises adding a hydrocarbon solvent thereto, azeotropically fractionally distilling all of the EDA from the said mixture, and fractionally distilling said N-alkylethylenediamine therefrom.

13. A process according to claim 12 wherein the hydrocarbon solvent is recovered from the azeotropic distillate and recycled to said mixture of N-alkylethylenediamine and EDA.

14. A process for preparing N-alkylethylenediamine according to claims 12 or 13 wherein said N-alkylethylenediamine is N-ethylethylenediamine.

15. A process according to claim 14 wherein the hydrocarbon solvent is n-heptane.

16. A process according to claim 1 further characterized in that the reaction mixture is prepared by reacting ethylenediamine with an alkyl halide, and in that the hydrocarbon solvent is added to the resulting ammonium salt from which EDA is removed by azeotropic distillation, and which is thereafter neutralized with an inorganic alkalizing agent to produce an organic phase and an inorganic halide, said organic phase being separated from said inorganic halide and being the phase in which residual EDA and water are removed by azeotropic distillation.

17. A process according to claim 16 for preparing N-alkylethylenediamine of about 99% purity comprising (a) reacting an alkyl halide and ethylendiamine (EDA) at a mole ratio of EDA to said alkyl halide of about 1–20 to 1, and at a temperature of about −10° C. to about 120° C. under anhydrous conditions to obtain an alkylation reaction mixture; (b) adding to said reaction mixture about 0.02–100% by weight of a suitable hydrocarbon solvent, based on the weight of said reaction mixture; (c) azeotropically fractionally distilling the EDA and said hydrocarbon solvent to essentially remove EDA; (d) neutralizing the resulting mixture by contacting it with at least 0.9 molecular equivalent of a suitable alkalizing agent, per mole of said alkyl halide, to form a slurry of an alkali halide precipitate; (e) separating said alkali halide precipitate from said slurry and recovering the resulting mother liquor; (f) washing said separated alkali halide with said hydrocarbon solvent; (g) azeotropically fractionally distilling a combination of said mother liquor from step (e) plus recovered hydrocarbon wash liquor from step (f) to remove essentially all water and residual EDA from the resulting mixture; and (h) fractionally distilling said resulting mixture to remove residual hydrocarbon solvent and recover said N-alkylethylenediamine.

18. A process according to claim 17 wherein said hydrocarbon is n-heptane.

19. A process according to claim 17 wherein step (a) is at a temperature of about 25° C. to about 75° C.

20. A process according to claim 17 wherein step (a) the mole ratio of EDA to said alkyl halide is about 2–5 to 1.

21. A process according to claim 17 wherein about 0.02–1.0% of said hydrocarbon, based on the weight of said reaction mixture is added in step (b).

22. A process according to claim 18 wherein about 0.02–1.0% of said n-heptane, based on the weight of said reaction mixture, is added in step (b).

23. A process according to claim 17 wherein the alkylizing agent of step (d) is about 50% aqueous sodium hydroxide.

24. A process for preparing N-ethylethylenediamine (NEED) according to claims 19 or 20 or 22 or 23 wherein said alkyl halide is selected from the group consisting of ethyl chloride, ethyl bromide or ethyl iodide.

25. A process according to claim 24 wherein said alkyl halide is ethyl chloride.

* * * * *